US 11,763,940 B2

(12) United States Patent
Juergens

(10) Patent No.: US 11,763,940 B2
(45) Date of Patent: Sep. 19, 2023

(54) MEDICAL DATA COMMUNICATION SYSTEM, TRACKING SYSTEM FOR MEDICAL DEVICES, AND METHOD FOR OPERATION THEREOF

(71) Applicant: OLYMPUS WINTER & IBE GMBH, Hamburg (DE)

(72) Inventor: Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 1054 days.

(21) Appl. No.: 16/351,760

(22) Filed: Mar. 13, 2019

(65) Prior Publication Data

US 2019/0214130 A1 Jul. 11, 2019

Related U.S. Application Data

(63) Continuation of application No. PCT/EP2017/072156, filed on Sep. 5, 2017.

(30) Foreign Application Priority Data

Sep. 14, 2016 (DE) .......................... 102016217556.4

(51) Int. Cl.
*G16H 40/60* (2018.01)
*A61B 90/90* (2016.01)
(Continued)

(52) U.S. Cl.
CPC ............. *G16H 40/60* (2018.01); *A61B 90/90* (2016.02); *G16H 40/40* (2018.01); *H04W 4/025* (2013.01)

(58) Field of Classification Search
CPC ........ G16H 40/60; A61B 90/90; H04W 4/025
(Continued)

(56) References Cited

U.S. PATENT DOCUMENTS

2009/0063187 A1   3/2009  Johnson et al.
2009/0312612 A1*  12/2009 Rantala ................ A61B 5/0205
                                            702/19
(Continued)

FOREIGN PATENT DOCUMENTS

CN       104011764 A       8/2014
JP       H10-276975 A     10/1998
(Continued)

OTHER PUBLICATIONS

Japanese Office Action dated Jun. 9, 2020 in Japanese Patent Application No. 2019-514222.
(Continued)

*Primary Examiner* — Paultep Savusdiphol
(74) *Attorney, Agent, or Firm* — Scully, Scott, Murphy & Presser, P.C.

(57) ABSTRACT

A medical data communication system including: at least one medical device; at least one wireless access point; and a central computer; wherein the at least one wireless access point and the central computer are coupled via a network; the at least one medical device comprises a logic module and a transmit/receive module coupled thereto; the transmit/receive module and the at least one wireless access point are configured to establish a wireless data link at least intermittently; and the logic module comprises at least one input interface to receive data, the logic module being configured to transmit the received data via the transmit/receive module and via the wireless data link to the access point.

10 Claims, 1 Drawing Sheet

(51) Int. Cl.
*G16H 40/40* (2018.01)
*H04W 4/02* (2018.01)

(58) Field of Classification Search
USPC .................................................. 235/451, 492
See application file for complete search history.

(56) References Cited

U.S. PATENT DOCUMENTS

| | | | |
|---|---|---|---|
| 2012/0173177 A1 | 7/2012 | Nishiyama et al. | |
| 2013/0104120 A1* | 4/2013 | Arrizza | G16H 20/17 717/173 |
| 2013/0304489 A1* | 11/2013 | Miller | G06Q 10/20 705/2 |
| 2014/0067143 A1 | 3/2014 | Chen et al. | |
| 2014/0080511 A1* | 3/2014 | Saitoh | H04W 4/33 455/456.1 |
| 2015/0045022 A1* | 2/2015 | Prechner | H04W 48/16 455/434 |
| 2015/0151051 A1* | 6/2015 | Tsoukalis | G16H 20/17 604/67 |
| 2015/0377934 A1 | 12/2015 | Choe et al. | |
| 2016/0187153 A1* | 6/2016 | Johnson | G01C 21/3632 701/500 |
| 2016/0260301 A1 | 9/2016 | Miller et al. | |
| 2017/0300653 A1* | 10/2017 | Hresko | G16H 40/60 |
| 2019/0223093 A1* | 7/2019 | Watfa | H04W 48/18 |

FOREIGN PATENT DOCUMENTS

| | | |
|---|---|---|
| JP | 2004-344216 A | 12/2004 |
| JP | 2006-051073 A | 2/2006 |
| JP | 2009-165706 A | 7/2009 |
| JP | 2011-239013 A | 11/2011 |
| JP | 2012-523944 A | 10/2012 |
| JP | 2013-539087 A | 10/2013 |
| JP | 2014-078932 A | 5/2014 |
| KR | 10-2013-0072450 A | 7/2013 |
| WO | WO 2011/012914 A1 | 2/2011 |
| WO | WO 2016/106132 A2 | 6/2016 |

OTHER PUBLICATIONS

International Search Report dated Nov. 15, 2017 issued in PCT/EP2017/072156.

* cited by examiner

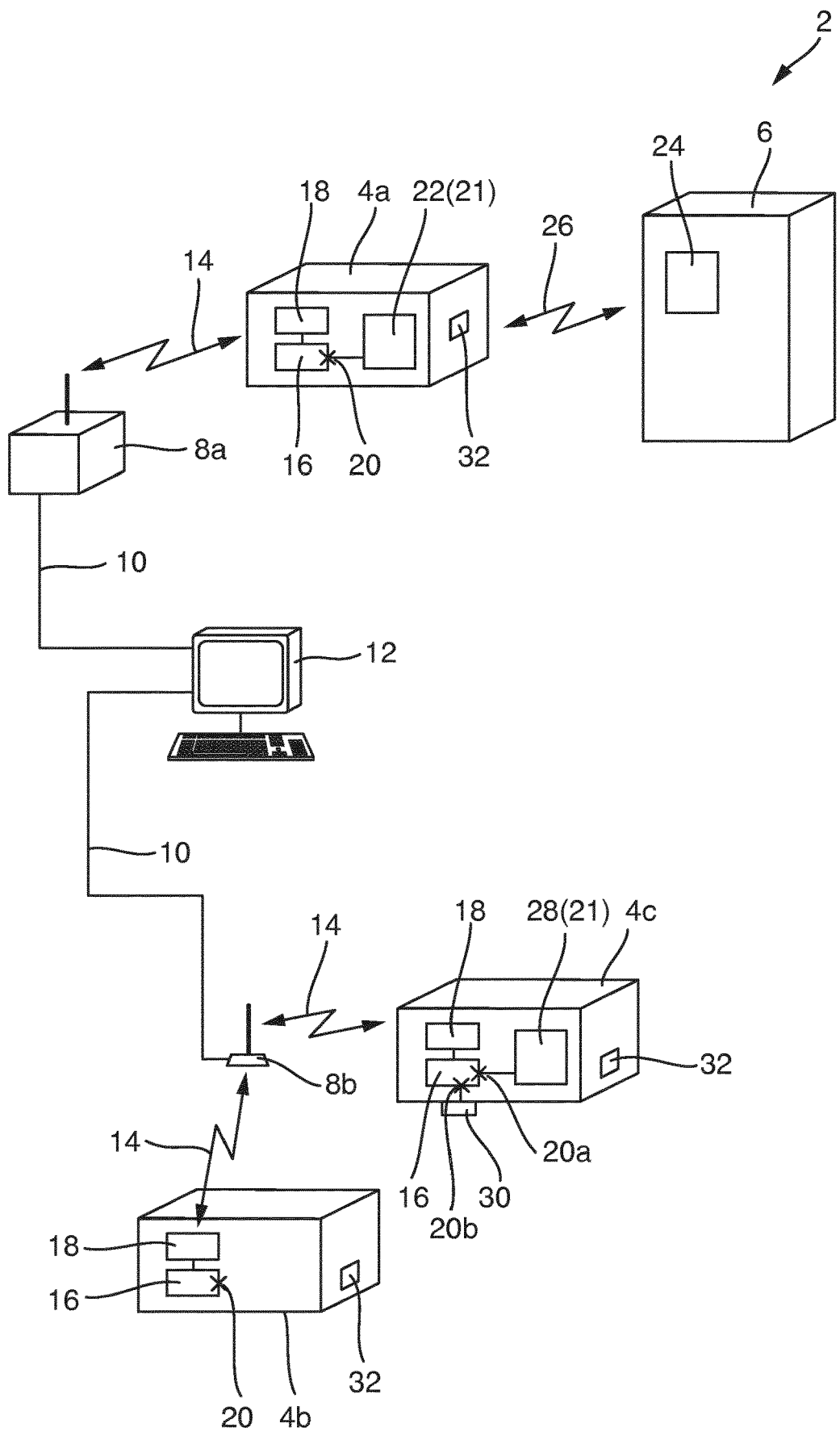

MEDICAL DATA COMMUNICATION SYSTEM, TRACKING SYSTEM FOR MEDICAL DEVICES, AND METHOD FOR OPERATION THEREOF

CROSS-REFERENCE TO RELATED APPLICATION

The present application is a continuation of PCT/EP2017/072156 filed on Sep. 5, 2017, which is based upon and claims the benefit to DE 10 2016 217 556.4 filed on Sep. 14, 2016, the entire contents of each of which are incorporated herein by reference.

BACKGROUND

Field

The present disclosure relates to a medical data communication system, an in particular to a medical data communication system comprising at least one medical device, at least one wireless access point, and a central computer, wherein the access point and the central computer are coupled via a network. The present disclosure additionally relates to a tracking system for medical devices. Furthermore, the present disclosure relates to a method for operation of a medical data communication system, an in particular to a method for operation of a medical data communication system which comprises at least one medical device, at least one wireless access point, and a central computer, wherein the access point and the central computer are coupled via a network. Further, the present disclosure relates to a method for tracking medical devices.

Prior Art

Medical devices, for example endoscopes, are frequently equipped with a RFID tag or a NFC tag, so that they can be simply and quickly identified. Medical peripheral devices such as, for example, a processing apparatus, are also frequently provided with such tags. An endoscope is, for example, identified fully automatically, if said endoscope is inserted into a processing apparatus. Such a processing apparatus (also frequently referred to as a cleaning and disinfection device) is, for example, known under the designation ETD in various versions from the manufacturer Olympus Winter & Ibe, Hamburg.

It is also known that medical peripheral devices such as, for example, a processing apparatus can be equipped with communication modules, so that they can exchange information with further devices. Modules which operate in accordance with one of the following standards: Bluetooth, Zigbee, WLAN (Wi-Fi), GPRS or UMTS are, for example provided as communication modules.

To set up a data link between the medical devices, it is necessary for the peripheral devices to be equipped with reading devices, for example a RFID reader, which are compatible with the tags used on the medical devices. However, each manufacturer of medical devices now uses its own communication standard and, in part, also tags using different technologies. To ensure that the peripheral medical devices can successfully communicate with as many medical instruments as possible, including those made by different manufacturers, considerable retrofitting and upgrading are in part required.

In addition, the communication technology used is, in many cases, not configured such that data can also be transmitted over greater distances. Thus, the wireless data links, which are frequently deployed and which operate in accordance with the Bluetooth, Zigbee or WLAN (Wi-Fi) standard, only have a very limited range. It is true that if other protocols, for example, GPRS or UMTS are deployed, it is possible to communicate over greater distances as well, however recourse must be is had to the public communication network for this.

SUMMARY

It is therefore an object to provide a medical data communication system, a tracking system for medical devices, a method for operation of a medical data communication system, as well as a method for tracking medical devices, which also has an improved ability to communicate over greater distances and is, in addition, flexible.

Such object is achieved by a medical data communication system, comprising at least one medical device, at least one wireless access point, and a central computer, wherein the access point and the central computer are coupled via a network, wherein the medical device can comprise a logic module and a transmit/receive module coupled thereto, wherein the transmit/receive module and the wireless access point can be configured to establish a wireless data link at least intermittently, and wherein the logic module can comprise at least one input interface to receive data and can be configured to transmit the received data via the transmit/receive module and via the wireless data link to the access point.

In the context of the present description, a "wireless access point" is an electronic device which functions as an interface for cordless communication terminals. Such devices are frequently referred to as a wireless access point or access point. The wireless access point can be a WLAN access point, as integrated into a WLAN router.

The data received at the input interface of the medical device can not only be transmitted to the access point, but can also be forwarded from there, such as, to the central computer. The network can provide the relevant infrastructure for the further data transmission between the access point and, to a further device, such as, the central computer. The data communication in this network can be effected in accordance with the usual protocols and standards, such as, TCP/IP.

The medical device can provide a bridge function. The data received at the interface can be forwarded and transmitted via an access point into the network (and from there, onwards, such as, to the central computer). The received data can be evaluated in the central computer. It is likewise provided that data from the central computer can be sent back to the medical device. In this case, the communication path is reversed, as described above. In connection with this, if multiple access points are comprised, each of these access points can attempt to set up a data link with the medical device. This considerably improves the probability of a corresponding data transmission taking place successfully.

Such a "broadcast principle" can also be deployed during the communication of individual medical devices with one another. Traditional ad-hoc networks are only possible where two medical devices are situated in the reception range of a single access point. An extended ad-hoc network can be provided if the medical devices communicate with one another using the network connecting the access points. They can be situated in the reception ranges of different access points but nevertheless, due to the communication taking place via all of the access points, act as if they were situated in the reception range of a single access point. Consequently, communication is also possible over distances which are greater than a typical reception and transmission radius of an access point.

The wireless data link between the transmit/receive module and the access point can lie in a frequency band between 850 MHz and 950 MHz, such as, between 867 and 869 MHz, between 902 and 928 MHz and/or between 920 and 925 MHz. The frequency band can also lie between 902.3 and 914.9 MHz, between 903 and 914.9 MHz and/or between 923.3 and 927.5 MHz. Multiple channels can be provided next to one another in each of the frequency bands.

A modulation method can be deployed which uses a CSS frequency spread (chirp spread spectrum). This type of modulation is robust and allows large ranges. Additionally, the energy consumption is low in the case of this type of modulation.

The medical device can comprise a data source coupled to the input interface, such as, a sensor. The data source can be an internal or an external data source. Therefore, data source can be situated inside or outside the medical device. A sensor can be provided as the data source, such as a sensor that captures internal and/or external parameters, such as, physical parameters.

A RFID or a NFC reader can be provided as the sensor. The medical device would therefore be enabled to communicate with other medical devices which are provided with RFID or NFC tags. The same applies to medical peripheral devices which can be provided with such tags.

The sensor can additionally be a temperature sensor, a pressure sensor, a humidity sensor, an acceleration sensor, an angular-velocity sensor, an angular acceleration sensor or the like. Thus, it is possible to measure these physical parameters which are captured inside and/or outside the medical device, and to transmit their measured values to the central unit. The sensor can be a measurement device for capturing an electrical voltage or an electrical current. These variables can, in turn, be captured internally and/or externally as well. An internal voltage level or an internally captured current intensity can characterize the operating state of the medical device. It can thus be ascertained whether said medical device is in active use at the moment or is in the process of being processed. The same also applies of course with respect to the capturing of the previously indicated physical parameters which can also give some indication of the current use of the medical device.

The internal interface of the medical device can be coupled to further electronic components of the medical device, so that information regarding the medical device or its status or operating state can be called up via the data provided at the interface. It is therefore possible to call up a serial number, a firmware version, the current operating state or the like.

All of this information allows the user of the medical data communication system to get a detailed idea of the medical devices available in this data communication system or communicating with the latter, as well as the medical peripheral devices. This facilitates the planning and optimization of the use or the deployment of these medical devices in a medical facility, such as, in a hospital.

According to another embodiment, the network can be a LAN or WAN network. The network, which can be wired, allows communication of individual medical devices or communication of the medical devices with one another and with the central unit over distances which are far greater than typical transmitting and receiving distances of a wireless access point. It is thus possible to achieve extensive networking of the medical devices in a medical facility. Extensive networking of the medical devices is made possible. The island structure of the ad-hoc communication networks, which otherwise frequently occurs in the case of wireless communication, is abolished.

According to another embodiment, the medical device can comprise an energy store, such as, a battery, for operating the logic module and the transmit/receive module. With the integration of the energy store in the medical device, said medical device is then able to communicate as well, if it is not connected to an external power supply, such as, in sleep mode (standby status) in a storeroom. The functionality of the network is thus considerably extended. Not only active, but also medical devices which are in sleep mode or even switched off can be located. A data link with these devices can be established.

A plurality of wireless access points and a plurality of medical devices can be provided, and each medical device can set up a data link with each access point, and can, access the central computer via each access point, and wherein the network, to which the access points and the central computer are coupled, can be a star-shaped network. A star-shaped construction of the network in favor of a mesh-like construction, in which individual mobile devices can forward, data from other mobile devices to an access point, can provide improved energy consumption of the individual medical devices. This is significantly lower compared with a netlike network structure, since the outlay for forwarding the data is dispensed with.

Such object can be additionally achieved by a tracking system for medical devices, which is installed in a medical facility, where the medical data communication system is comprised according to one or more of the previously indicated aspects, which comprises a plurality of wireless access points and a plurality of medical devices. The network of this data communication system can couple a plurality of access points installed in the medical facility to one another. The central computer is configured to determine a location and/or a path of this medical device in the medical facility on the basis of the data received at the input interface of the transmit/receive module of a specific medical device and forwarded to the central computer.

Such a tracking system is frequently also referred to as an asset tracking system. The information transmitted to the central computer regarding the location or the path of the medical device in the medical facility can allow optimized planning with respect to the deployment and the use of the medical devices.

In connection with this, the location can be determined, such as, on the basis of the data which are captured by a sensor connected to the interface of the medical device. The term "path" of the medical device can be understood within the context of the present description to be a piece of information which indicates that the medical device was being deployed at a first point in time at a specific first location (such as, an operating theater), was being processed at a second point in time at a second location (such as, in a processing apparatus) and then stored at a third point in time at a third location, such as, in a supply cabinet. Consequently, the usage history of the medical device can be perfectly comprehensible on the basis of its "path". This makes it possible to plan or initiate servicing which is to be performed at regular intervals.

Such object can be, in addition, achieved by a method for operation of a medical data communication system, which comprises at least one medical device, at least one wireless access point, and a central computer, wherein the access point and the central computer are coupled via a network, wherein the method is further developed in that the medical device comprises a logic module and a transmit/receive module coupled thereto, wherein the transmit/receive module and the wireless access point establish a wireless data link at least intermittently, and wherein the logic module comprises at least one input interface, at which data are received, wherein these data are transmitted via the transmit/receive module and via the wireless data link to the access point.

The same or similar advantages apply to the method for operation of the medical data communication system, as have already been indicated with respect to the medical data communication system, so that repetitions shall be dispensed with.

According to an embodiment, the wireless data link between the transmit/receive module and the access point can be operated in a frequency band between 850 MHz and 950 MHz. The input interface can be coupled to a data source of the medical device and receive data produced by the data source, such as, data produced by a sensor. According to another embodiment, the medical device can comprises an energy store, such as, a battery, and the logic module and the transmit/receive module can be supplied by the energy store.

The method can also be further developed in the same or a similar way in accordance with the advantageous aspects indicated with respect to the medical data communication system.

Such object can be additionally achieved by a method for tracking medical devices in a medical facility. This method can be further developed in that a medical data communication system is installed in the medical facility, which comprises a plurality of wireless access points and a plurality of medical devices. The network of this data communication system can couple the plurality of the installed access points to one another. The medical data communication system can be operated according to a method for operation of a medical data communication system according to one or more of the previously indicated aspects. A location and/or a path of the medical device in the medical facility can be determined in the central computer on the basis of the data received at the input interface of the transmit/receive module of a specific medical device and forwarded to the central computer.

The same or similar advantages apply to the method for tracking medical devices, as have already been indicated with respect to the tracking system for medical devices, so that repetitions shall be dispensed with.

Further features will become evident from the description of embodiments, together with the claims and the appended drawing. Embodiments can fulfill individual features or a combination of several features.

BRIEF DESCRIPTION OF THE DRAWING

The embodiments are described below without limiting the general concept of the invention by means of exemplary embodiments with reference to the drawing, wherein reference is expressly made to the drawing regarding all of the details which are not explained in greater detail in the text, wherein:

the FIGURE shows a medical data communication system, which is also configured as a tracking system for medical devices, in a schematic representation.

In the drawing, the same or similar elements and/or parts are, in each case, provided with the same reference numerals so that they are not introduced again in each case.

DETAILED DESCRIPTION

The FIGURE shows a medical data communication system 2, which comprises multiple medical devices 4a, 4b, 4c as well as, in addition, by way of example, a medical peripheral device 6. Additionally, the medical data communication system 2 comprises multiple wireless access points 8a, 8b, which are connected to one another as well as to a central computer 12 via a network 10. The medical devices 4a, 4b, 4c can be, for example, endoscopes, imaging medical devices, HF surgical devices or the like.

The central computer 12 is, for example, a PC or a workstation. The medical peripheral device 6 is, for example, a processing apparatus. The communication in the network 10 is effected, for example, in accordance with the TCP/IP standard. The medical devices 4a, 4b, 4c are connected via wireless data links 14 to the wireless access points 8a, 8b.

Each medical device 4a, 4b, 4c comprises a logic module 16 which is, in each case, coupled to a transmit/receive module 18. The respective transmit/receive modules 18 each establish the wireless data links 14 to one of the wireless access points 8a, 8b. The logic module 16 comprises, in each case, at least one input interface 20, 20a, 20b to receive data. The logic module 16 is configured to transmit the data received at this input interface 20, 20a, 20b via the transmit/receive module 18 and via the wireless data link 14 to the respective access point 8a, 8b.

The input interface 20, 20a, 20b is connected, in the case of the medical devices 4a, 4b, 4c represented in the FIGURE, in each case to another data source, by way of example, which are explained below.

In the case of the medical device 4a, the input interface 20 is connected to a reader 22 for wirelessly reading out a characterizing feature 24. For example, the reader 22 is a RFID reader which reads out the RFID tag deployed, by way of example, as a characterizing feature 24 and situated on the medical peripheral device 6. To this end, a short-range wireless data link 26 is established between the reader 20 and the characterizing feature 24. The reader 20 shall be generally regarded as a sensor 21.

The medical peripheral device 6 is, for example, an autoclave, a storage cabinet or a processing device for processing a medical device 4a, 4b, 4c. For example, the characterizing feature 24 on the medical peripheral device 6 is read out from the medical device 4a the moment that this is positioned in the medical peripheral device 6. For example, this means that an endoscope reads out the characterizing feature 24 on a storage cabinet when this is placed in the storage cabinet. By transmitting the relevant information to the central computer 12, it can be ascertained, for example, that said endoscope is situated in the relevant storage cabinet.

In the case of the medical device 4c, the first input interface 20a is connected to a measurement unit 28, which allows it, for example, to capture physical parameters. Such a measurement unit 28 is also generally regarded as a sensor 21. The measurement unit 28 is, for example, a temperature sensor, a pressure sensor, a humidity sensor, an acceleration sensor, an angular-velocity sensor, an angular acceleration sensor or the like. A combination of these sensors is also provided.

The second input interface 20b is connected to an external interface 30 which is situated, for example, on an outer side of the housing of the medical device 4c. Further medical devices can be coupled to the external interface 30, for example. It is also possible to use the medical device 4c as a module for transmitting data, since this is in a position to transmit the data received at the external interface 30 and, consequently, also at the input interface 20b, for example, to the central computer 12.

The values of the physical parameters, which are captured with the aid of the measurement unit 28, can also be transmitted to the central computer 12. An evaluation of these measurement values allows a conclusion to be drawn regarding the current use or an operating state of the medical device 4c. For example, specific temperatures and humidity values are characteristic of a processing process. If these are measured, it can for example be concluded that the endoscope is currently being processed.

The medical device 4b comprises an input interface 20 which involves an internal interface. Data from the medical device 4b can be received at said interface, for example regarding a hardware number, a firmware version or the like. It is also possible to call up, for example, an error memory of the medical device 4b and to transmit these data via the input interface 20 to the central computer 12.

The medical devices 4a, 4b, 4c additionally each comprise an energy store 32, for example a battery. Thus, it is possible to establish the respective wireless data link 14, even if the medical devices 4a, 4b, 4c are not connected to a power supply. The energy available in the energy store 32 can be used to operate the logic module 16 and the transmit/receive module 18.

The wireless data links 14 between the respective transmit/receive module 18 and the access points 8a, 8b lie in a frequency band between 850 MHz and 950 MHz. Multiple uplink channels and multiple downlink channels can be provided, wherein a chirp spread spectrum modulation (CSS modulation) can be deployed as the modulation method.

Each of the medical devices 4a, 4b, 4c can communicate with each of the access points 8a, 8b. Conversely, each access point 8a, 8b endeavors to enter into contact with each of the medical devices 4a, 4b, 4c as well. Corresponding signals are, for example, sent out by all access points 8a, 8b. Finally, the access points 8a, 8b can be connected in a star-shaped network 10 to the central computer 12.

According to another aspect, a tracking system is provided for medical devices 4a, 4b, 4c. Such a tracking system is installed in a medical facility, for example a hospital. The tracking system comprises a medical data communication system 2, as is shown by way of example in the FIGURE. The network 10 of such a data communication system 2, which forms the basis of the tracking system, comprises a plurality of access points 8a, 8b, which are installed in the medical facility, and are coupled to one another via the network 10. The central computer 12 is configured to determine a location and/or a path of this medical device 4a, 4b, 4c in the medical facility on the basis of the data received at the respective input interface 20, 20a, 20b of the transmit/receive module 18 of a specific medical device 4a, 4b, 4c and forwarded to the central computer 12.

The medical device 4a comprises, as a sensor 21, by way of example, a reader 22, additionally for example a RFID reader or a NFC reader, which is connected to the logic module 16. A medical peripheral device 6, for example a processing device (CDS system), a steam autoclave or the like is equipped with RFID tag or a NFC tag as a machine-readable characterizing feature 24. If the medical device 4a is inserted into such a system, as constituted by the medical peripheral device 6, the medical device 4a identifies the peripheral device 6 by reading out the characterizing feature 24. This information is transmitted via the transmit/receive module 18 and via the wireless data link 14 to the wireless access point 8a and from there onwards via the network 10 to the central computer 12.

It is ascertained in the central computer 12 on the basis of the available information that the medical device 4a is situated at that moment, for example, in a specific processing device, the characterizing feature 24 of which has just been read out. The medical device 4a can thus be located in the medical facility. In addition, various steps (and consequently a path of the medical instrument 4a), which the medical device 4a runs through during its use in the medical facility, can, for example, be documented.

If, for example, a storage cabinet is likewise provided with a machine-readable characterizing feature 24 as a further medical peripheral device 6, which is not represented, it can be concluded, if the corresponding information thereof (for example an inventory number) is received in the central computer 12 that the medical device 4a is at that moment situated in the storage cabinet. It is also possible, for example, to provide the baskets of a processing system with corresponding machine-readable characterizing features 24, such that the individual contents of an individual cleaning basket can be captured in the central computer 12.

Similar information can also be obtained if, in the case of the medical device designated with 4c, the sensor 21 of which is a measurement unit 28, the measuring variables captured by said sensor are evaluated in the central computer 12. At the same time, the status of the medical device 4c can be characterized on the basis of these measuring variables. For example, a message is sent, if one or more of the measuring variables already indicated previously falls below a pre-determined boundary value. It can additionally be provided that a message is produced, if information is received at an external interface 30.

The medical device 4c can transmit corresponding messages periodically, so that the current position or use can be concluded on the basis of a course of the measurement values captured in each case. For example, activity cycles, reprocessing cycles, number of uses or the like can be determined on the basis of these measurement values. The same applies of course to a medical device 4a, in which the relevant information regarding its use is obtained on the basis of machine-readable characterizing features 24. It is also possible to carry out usage-based billing (pay per use) for the medical devices 4a, 4b, 4c.

Additionally, it is for example provided that the medical device designated with 4b monitors itself on the basis of the information received at an internal interface 20. An error memory can, for example, be read out or a necessary processing or maintenance can be displayed. In addition, a hardware version or firmware version of the medical device 4b can be called up and monitored in real time.

In one method for operation of a medical data communication system 2, as shown in the FIGURE, the transmit/receive module 18 establishes a wireless data link 14 to a wireless access point 8a, 8b at least intermittently. The data received at an input interface 20, 20a, 20b are transmitted by the logic module 16 via the transmit/receive module 18 and via the wireless data link 14 to an access point 8a, 8b. From there, the data are transmitted onwards via the network 10 to a central computer 12.

In one method for tracking medical devices 4a, 4b, 4c in a medical facility, for example a hospital, in which a medical data communication system 2 is installed, as shown by way of example in the FIGURE, the data transmitted by the medical devices 4a, 4b, 4c to the central computer 12 are evaluated. A conclusion is drawn from this regarding a location and/or a path of the medical device(s) 4a, 4b, 4c in the medical facility.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Medical data communication system
4a, 4b, 4c Medical devices
6 Medical peripheral device
8a, 8b Wireless access points
10 Network
12 Central computer
14 Wireless data link
16 Logic module
18 Transmit/receive module
20, 20a, 20b Input interfaces
21 Sensor
22 Reader
24 Characterizing feature
26 Short-range data link
28 Measurement unit
30 External interface
32 Energy store

What is claimed is:

1. A medical data communication system comprising:
at least one medical device;
at least one wireless access point; and
a central computer;
wherein the at least one wireless access point and the central computer are coupled via a network;
the at least one medical device comprises a logic module and a transmit/receive module coupled thereto;
the transmit/receive module and the at least one wireless access point are configured to establish a wireless data link at least intermittently; and
the logic module comprises at least one input interface to receive data, the logic module being configured to transmit the received data via the transmit/receive module and via the wireless data link to the access point;
wherein the at least one wireless access point comprises a plurality of wireless access points and the at least one medical device comprises a plurality of medical devices, each of the plurality of medical devices being configured to set up a data link and communicate with each of the plurality of wireless access points;
each of the plurality of medical devices are configured to access the central computer via each of the plurality of wireless access points;
the at least one medical device comprises an energy store for operating the logic module and the transmit/receive module;
the at least one medical device is configured to communicate with the plurality of wireless access points in a sleep mode or when switched off by supplying the transmit/receive module with energy from the energy store; and
the network, to which the plurality of wireless access points and the central computer are coupled is configured as a star-shaped network, wherein in the star-shaped network, the plurality of medical devices do not directly communicate among each other and the plurality of wireless access points do not directly communicate among each other.

2. The medical data communication system according to claim 1, wherein the wireless data link between the transmit/receive module and the at least one wireless access point lies in a frequency band between 850 MHz and 950 MHz.

3. The medical data communication system according to claim 1, wherein the at least one medical device comprises a data source coupled to the input interface.

4. The medical data communication system according to claim 3, wherein the data source comprises a sensor.

5. The medical data communication system according to claim 1, wherein the network is one of a LAN and WAN network.

6. The medical data communication system according to claim 1, wherein the energy store comprises a battery.

7. A tracking system for medical devices, which is installed in a medical facility, the tracking system comprises:
a medical data communication system according to claim 1, the network of which couples the plurality of wireless access points installed in the medical facility to one another;
wherein the central computer is configured to determine one or more of a location and a path of a specific medical device of the plurality of medical devices in the medical facility on the basis of data received at the input interface of the transmit/receive module of the specific medical device and forwarded to the central computer.

8. A method for operation of a medical data communication system, which comprises at least one medical device, at least one wireless access point, and a central computer, wherein the at least one wireless access point and the central computer are coupled via a network, the at least one medical device comprises a logic module and a transmit/receive module coupled thereto, the method comprising:
establishing at least an intermittent data link between the transmit/receive module and the at least one wireless access point; and
wherein the logic module comprises at least one input interface, at which data is received, the method further comprising transmitting the data via the transmit/receive module and via the wireless data link to the at least one wireless access point;
wherein the at least one wireless access point comprises a plurality of wireless access points and the at least one medical device comprises a plurality of medical devices, each of the plurality of medical devices being configured to set up a data link and communicate with each of the plurality of wireless access points;
each of the plurality of medical devices are configured to access the central computer via each of the plurality of wireless access points;
the at least one medical device comprises an energy store for operating the logic module and the transmit/receive module;
the at least one medical device is configured to communicate with the plurality of wireless access points in a sleep mode or when switched off by supplying the transmit/receive module with energy from the energy store; and the network, to which the plurality of wireless access points and the central computer are coupled is configured as a star-shaped network, wherein in the star-shaped network, the plurality of medical devices do not directly communicate among each other and the plurality of wireless access points do not directly communicate among each other.

9. The method according to claim 8, comprising operating the wireless data link between the transmit/receive module and the at least one wireless access point in a frequency band between 850 MHz and 950 MHz.

10. The method according to claim 8, comprising coupling the input interface to a data source of the at least one medical device and receiving data produced by the data source.

* * * * *